United States Patent [19]
Ohno et al.

[11] Patent Number: 4,973,426
[45] Date of Patent: Nov. 27, 1990

[54] OPTICALLY ACTIVE COMPOUND HAVING A PLURALITY OF ASYMMETRIC CARBON ATOMS

[75] Inventors: Kouji Ohno; Shinichi Saito; Hiromichi Inoue; Kazutoshi Miyazawa, all of Yakohamashi; Makoto Ushioda, Kawasakishi, all of Japan

[73] Assignee: Chisso Corporation, Osaka, Japan

[21] Appl. No.: 160,279

[22] Filed: Feb. 25, 1988

[30] Foreign Application Priority Data

Mar. 4, 1987 [JP]  Japan ................... 62-49796

[51] Int. Cl.$^5$ ............ C09K 19/12; C09K 19/34; G02F 1/13; C07C 69/66
[52] U.S. Cl. ............ 252/299.66; 252/299.6; 252/299.61; 252/299.01; 350/350 S; 560/187; 560/141; 560/227; 560/228
[58] Field of Search ............ 350/350 S; 252/299.01, 252/299.61, 299.63, 299.66; 560/141, 157, 227, 228, 187

[56] References Cited

U.S. PATENT DOCUMENTS

| 4,592,858 | 6/1986 | Higuchi et al. ............ 252/299.66 |
| 4,725,688 | 2/1988 | Taguchi et al. ............ 252/299.61 |
| 4,744,918 | 5/1988 | Hepple et al. ............ 252/299.61 |

FOREIGN PATENT DOCUMENTS

| 0175591 | 3/1986 | European Pat. Off. . |
| 255219 | 2/1988 | European Pat. Off. . |
| 3515373 | 11/1986 | Fed. Rep. of Germany . |
| 2161808 | 1/1986 | United Kingdom . |
| 87/05012 | 8/1987 | World Int. Prop. O. . |
| 87/05018 | 8/1987 | World Int. Prop. O. . |

*Primary Examiner*—John S. Maples
*Assistant Examiner*—Philip Tucker
*Attorney, Agent, or Firm*—Wenderoth, Lind & Ponack

[57] ABSTRACT

An optically active compound having particularly a specific feature of increasing spontaneous polarization value as one of important specific features for ferroelectric liquid crystal compositions, and a ferroelectric liquid crystal composition containing the compound are provided, which compound is expressed by the formula $$R^1-\text{A}-\text{B}-O(CH_2)_l\overset{CH_3}{\underset{*}{CH}}(CH_2)_m O\overset{O}{\underset{\|}{C}}-R^2 \quad (I)$$

wherein $R^1$ represents a linear or branched chain alkyl, alkoxy, alkanoyl, alkoxycarbonyl or alkoxycarbonyloxy each of 1-15C, H, halogen or -CN; $R^2$ represents an optically active group having 2-20 skeletal atoms, -A- and -B- each represent

[ring structures with X substituents: various pyridyl, pyrimidinyl, pyridazinyl, phenyl, and cyclohexyl groups]

wherein X represents H, halogen or -CN; l represents an integer of 1-10; m is 0 or 1; and * indicates asymmetric C.

8 Claims, No Drawings

OPTICALLY ACTIVE COMPOUND HAVING A PLURALITY OF ASYMMETRIC CARBON ATOMS

BACKGROUND OF THE INVENTION

1. Field of the Invention

This invention relates to a novel organic compound and a liquid crystal composition containing the same. More particularly it relates to an organic compound having an optically active group and being useful as a component of ferroelectric liquid crystal compositions, and a ferroelectric liquid crystal composition containing the same.

2. Description of the Related Art

At present, TN (twisted nematic) display mode has been most broadly used as liquid crystal display elements and this TN liquid crystal display has a number of advantages such as low driving voltage, small power consumption, etc. However, it is inferior in the aspect of the response rate to emissive mode display elements such as cathode ray tube, electroluminescence, plasma display, etc. Further, a novel TN mode display element having its twist angle enlarged up to 180°-270° has also been developed, but it is still inferior in the aspect of the response rate As described above, efforts of various improvements have so far been made, but those having fully satisfactory performances have not yet been obtained. However, a novel display mode utilizing ferroelectric liquid crystals, the research of which has recently been extensively made, has a possibility of notably improving the response rate (Clark et al; Applied Phys. lett., 36, 899 (1980)). This mode utilizes chiral smectic phases such as chiral smectic C phase (hereinafter abbreviated to SC*). It is known that the phases exhibiting ferroelectric properties are not only limited to SC* phase, but phases of chiral smectic F, G, H, I, etc. also exhibit ferroelectric properties.

A number of specific features are required for ferroelectric liquid crystal materials to be practically used for ferroelectric liquid crystal display elements, but at present, there is no single compound which satisfies the requirements; hence it is necessary to use ferroelectric liquid crystal compositions obtained by mixing some liquid crystal compounds or non-liquid crystal compounds therewith.

SUMMARY OF THE INVENTION

The present inventors have found a compound having a specific feature of enhancing the spontaneous polarization value Ps as one of important specific features necessary for ferroelectric liquid crystal compositions.

The present invention resides in an optically active compound expressed by the formula

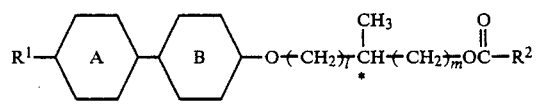
(I)

wherein $R^1$ represents a linear or branched chain alkyl group, alkoxy group, alkanoyl group, alkanoyloxy group, alkoxycarbonyl group or alkoxycarbonyloxy group each of 1 to 15 carbon atoms, hydrogen atom, a halogen atom or cyano group; $R^2$ represents an optically active group having 2 to 20 skeletal atoms in its chain;

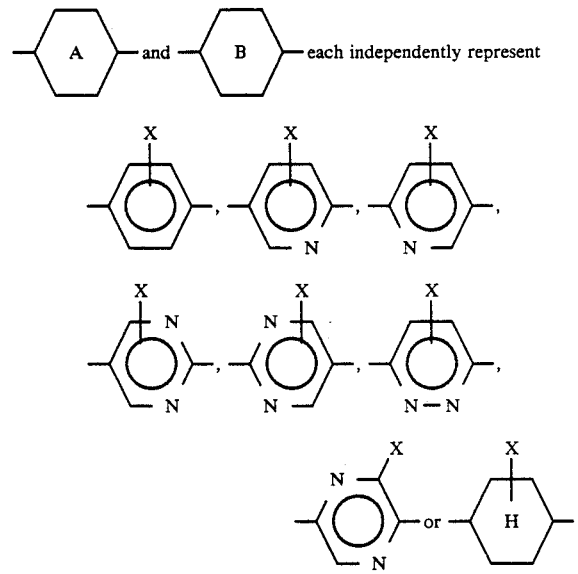

wherein X represents hydrogen atom, a halogen atom or cyano group; l represents an integer of 1 to 10; m represents 0 or 1; and * indicates an asymmetric carbon atom, and a chiral liquid crystal composition containing the compound.

DETAILED DESCRIPTION OF PREFERRED EMBODIMENTS

In the above formula (I), $R^1$ is preferably a linear chain alkyl group or alkoxy group each of 4 to 14 carbon atoms.

Representative examples of the optically active group $R^2$ are an optically active monohalogenated alkyl group or an alkyl group having an alkoxy branch each of 2 to 20 carbon atoms. Examples of the monohalogenated alkyl group are

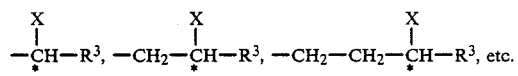

In these formulas, X represents F, Cl or Br; and $R^3$ represents a linear or branched chain alkyl group each of 1 to 15 carbon atoms and when $R^3$ represents a branched chain alkyl group, it may be an optically active group. Preferred examples of $R^2$ wherein $R^3$ represents a linear chain alkyl group and X represents a halogen atom are

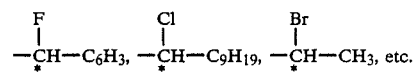

Further, preferred examples of $R^2$ wherein $R^3$ represents an optically active alkyl group and X represents a halogen atom are

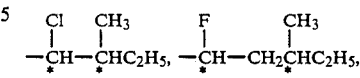

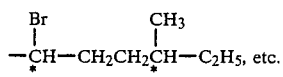

Further, preferred examples of R² in the case of an alkyl group having an alkoxy branch are

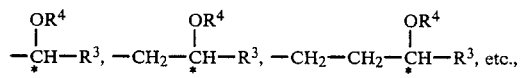

wherein R³ is as defined above and R⁴ represents a linear or branched chain alkyl group each of 1 to 10 carbon atoms and when R⁴ represents a branched chain alkyl group, R⁴ may be an optically active group. Preferred examples of R² wherein R³ and R⁴ are both a linear chain alkyl group are

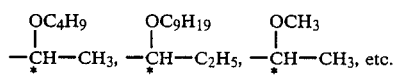

Preferred examples of R² wherein R⁴ represents an optically active alkyl group are

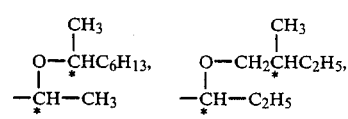

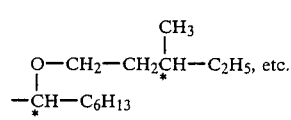

Preferred examples of R² wherein R³ represents an optically active alkyl group and R⁴ represents a linear chain alkyl group are

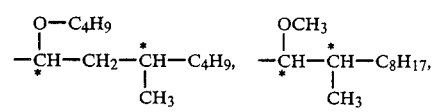

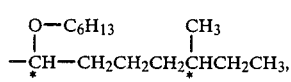

etc.

Preferred examples of R² wherein R³ and R⁴ both represent an optically active alkyl group are

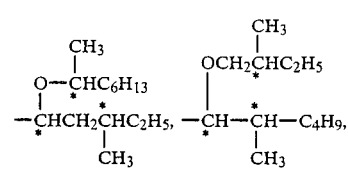

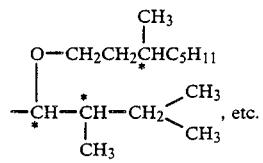

Further, preferred examples of

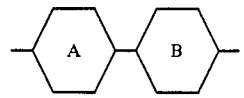

are

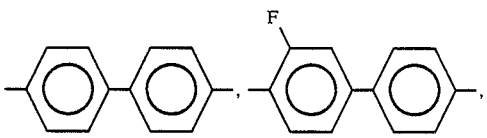

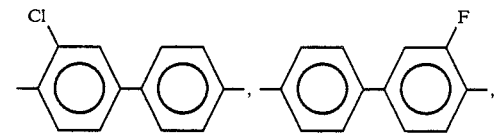

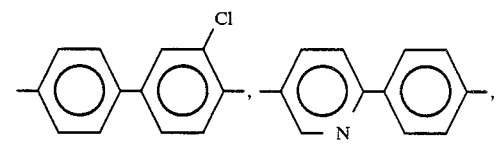

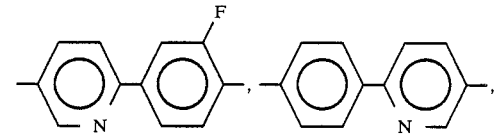

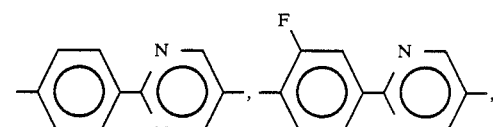

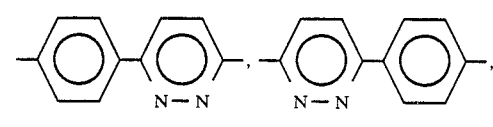

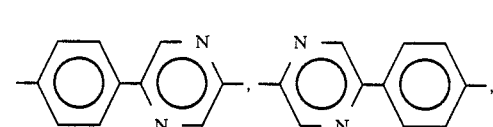

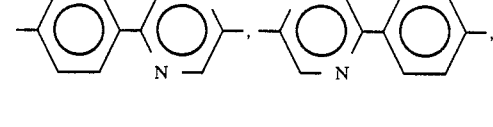

-continued

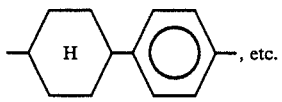, etc.

Among these, more preferred examples are

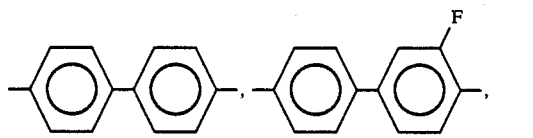

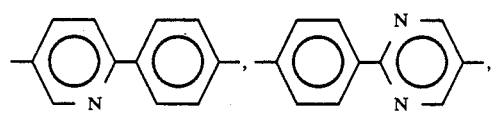

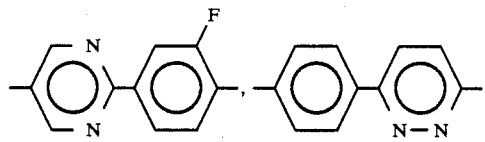

and

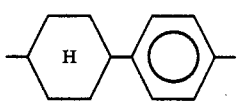

The specific feature of the compound expressed by the formula (I) of the present invention consists in that the compound has a large spontaneous polarization value (Ps) or potential spontaneous polarization value.

According to the measurement of the present inventors, for example when the Ps value of the compound of Example 1 mentioned below,

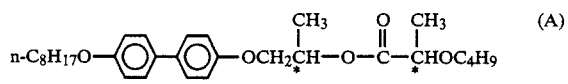

was measured by a extrapolation method, it amounted to 94 nC/cm$^2$ at 25° C. Since this value was not obtained by measuring the compound itself, it cannot be said that this value is the Ps of the compound itself, but in the case of practical use, compounds having such an effectiveness are very useful.

On the other hand, the Ps of a compound disclosed in Japanese patent application No. Sho 61-133269, the invention of which has also been made by the present inventors, and expressed by the formula

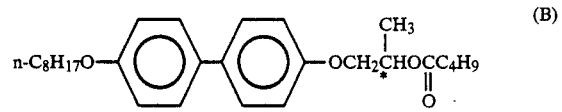

was measured to give 57 nC/cm$^2$ at 25° C. The Ps value of the compound (A) having the linear chain acyl group of the compound (B) converted into an optically active substituent acyl group became about twice that of the compound (B). Namely, when one more asymmetric carbon atom was introduced into the compound (B), the Ps value was notably increased. Thereby a ferroelectric composition containing the compound of the formula (I) of the present invention in an amount of 10% by weight can realize a response time as short as 100 μsec at 25° C.

Further, when the compound of the formula (I) of the present invention in a suitable quantity is added to a chiral or achiral smectic liquid crystal compound or a chiral smectic liquid crystal composition, it is possible to notably increase their Ps values.

The absolute configurations of the respective asymmetric carbon atoms in the formula (I) may be either of (R)-configuration or (S)-configuration.

When the compound of the present invention is added to a nematic liquid crystal composition, the resulting chiral nematic liquid crystal composition has a very short chiral pitch as illustrated in the Examples; hence the compound can be said to be very useful as a pitch-adjusting agent for chiral nematic liquid crystal compositions. Further, its temperature-dependency δP is small as illustrated in the Examples. The δP of (S)-4-(2'-methylbutyl)-4'-cyanobiphenyl as one of currently known pitch-adjusting agents is 0.543 under the same conditions; hence, even as compared therewith, it is seen that the δP of the compound of the present invention is small. In the case of the so-called super TN mode display having the twist angle enlarged up to 180°–270°, since a large temperature-dependency of pitch notably reduces its display quality, the temperature-dependency of pitch is preferred to be smaller. When a chiral nematic liquid crystal composition obtained by adding the compound of the present invention is used for a super TN mode display, the temperature-dependency of pitch is small; hence it is possible to prepare a superior super TN mode element having a small reduction in the display quality.

The compound of the formula (I) may be prepared for example through the following route:

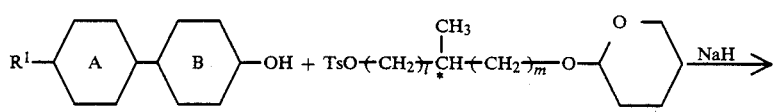

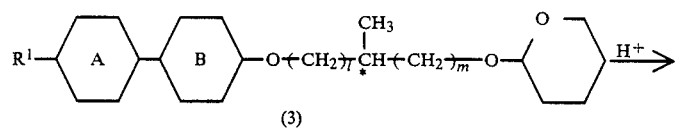

-continued

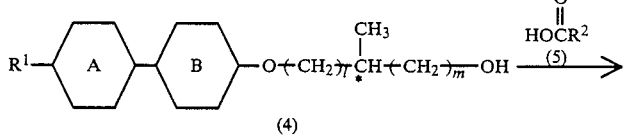

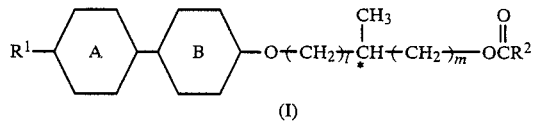

Using various combinations of compounds corresponding to the compound (1) with compounds corresponding to the compound (5), various compounds of the formula (I) may be obtained.

The compound and liquid crystal composition of the present invention will be described in more detail by way of the following Examples.

EXAMPLE 1

Preparation of (2'S, 2''S)-4'-octyloxy-4-(2'-(2'''-butoxypropionyloxy)-propoxy)biphenyl (a compound of the formula (I) wherein $R^1$ = octyloxy group;

group; —A—B— = —⟨○⟩—⟨○⟩—; l = 1; m = 0; and $R^2 = -\overset{*}{C}H(CH_3)OC_4H_9$, i.e.,

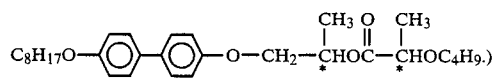

(i) Preparation of (S)-1-(4'-octyloxy-4-biphenyloxy)-propan-2-ol

A mixture of (2S)-2-tetrahydropyranyloxy-1-hydroxypropane (137 g, 0.85 mol) prepared according to the literature (C. Malanga et al, Synthetic Communications, 12 (1), 67–70 (1982)) with anhydrous pyridine (600 g) was cooled with ice, followed by dropwise adding to the mixture, a solution of p-toluenesulfonyl chloride (165 g, 0.87 mol) in pyridine (200 ml), agitating the mixture at 0° C. for 2 hours, successively agitating it at room temperature for 2 hours, allowing it to stand overnight, adding toluene (1 l), further adding 2N-NOH aqueous solution (500 ml), separating the resulting organic layer, several times washing it with water to make it neutral, drying it over MgSO₄ and distilling off the solvent, to obtain (2S)-2-(2'-tetrahydropyranyloxy)-1-(p-toluenesulfonyloxy)-propane (257 g; yield 95.9%).

A solution of (2S)-2-(2'-tetrahydropyranyloxy)-1-(p-toluenesulfonyloxy)-propane (20 g) in N,N-dimethylformamide (hereinafter abbreviated to DMF) (300 ml) was added to a mixture of sodium hydride (60%) (2 g), 4-hydroxy-4'-octyloxy-biphenyl(10 g) and tetrahydrofuran (hereinafter abbreviated to THF) (200 ml), followed by agitating the resulting mixture at 60° C. for 4 hours, allowing it to cool down to room temperature, adding toluene (300 ml) and water (300 ml), separating the resulting organic layer, washing it with an alkali solution and then with water, concentrating it, adding ethanol (300 ml) and pyridium p-toluenesulfonate (hereinafter abbreviated to PPTS) (2 g), agitating the mixture at 50° C. for 3 hours, distilling off ethanol, adding toluene (300 ml), washing the resulting organic layer with water, concentrating it and recrystallizing the concentrate, to obtain (S)-1-(4'-octyloxy-4-biphenylyloxy)-propan-2-ol (8 g).

(ii) Preparation of (S)-2-butoxypropionic acid

Silver oxide (77.5 g, 0.3 mol) was added to a mixture of (S)-(+)-ethyl lactate (49.4 g, 0.4 mol) with 1-iodobutane (100 g, 0.5 mol) over 2 hours, followed by allowing the mixture to stand at room temperature for 3 days, adding ether (30 ml) for dilution, filtering the resulting mixture, distilling off ether, washing the residue with 2N-NaOH aqueous solution, drying it over anhydrous MgSO₄ and distilling under reduced pressure, to obtain (S)-ethyl 2-butoxypropionate (30.7 g, b.p. 64° C./7 mmHg), adding thereto 5N-NaOH aqueous solution (50 ml), agitating the mixture at room temperature for 5 hours, pouring it in 6N-hydrochloric acid (75 ml) to extract the resulting organic layer with ether, washing the resulting organic layer with water and distilling off ether, to obtain (S)-2-butoxypropionic acid (21. 4 g).

Further, using (R)-methyl lactate as raw material, (R)-2-butoxypropionic acid was similarly obtained.

(iii) Preparation of the objective compound

To dichloromethane (500 ml) were added N,N-dicyclohexylcarbodiimide (hereinafter abbreviated to DCC) (13.0 g, 0.05 mol), 4-N,N'-dimethylaminopyridine (hereinafter abbreviated to DMAP) (2.0 g), (S)-1-(4'-octyloxy-4-biphenyloxy)-propan-2-ol (13.0 g) obtained in (i) and (S)-2-butoxypropionic acid (2.0 g) obtained in (ii), followed by agitating the mixture at room temperature for 5 hours, filtering off deposited crystals, washing the filtrate with 6N-hydrochloric acid, then with 2N-NaOH aqueous solution and further with water until the washing water became neutral, distilling off dichloromethane and recrystallizing the residue from ethanol, to obtain (2'S, 2''S)-4'-octyloxy-4-(2'-(2''-butoxypropionyloxy)-propoxy)biphenyl (8.0 g, m.p. 50.0° C.).

The above process was repeated except that (S)-(+)-ethyl lactate was replaced by (R)-(−)-ethyl lactate to obtain (2'S, 2''R)-4'-octyloxy-4-(2'(2''-butoxypropionyloxy)-propoxy)biphenyl (m.p. 41.0° C.).

EXAMPLE 2

Preparation of 4'-octyloxy-4-(2'-(2''-chloro-3''-methylvaleryloxy)-propoxy)biphenyl (a compound of the formula (I) wherein $R^1$=octyloxy group;

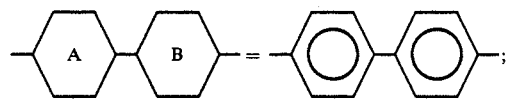

$l=1$; $m=0$; and

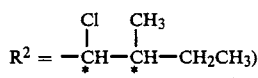

(i) Preparation of (2S,3S)-2-chloro-3-methylvaleric acid

L-isoleucine (105 g) was added to 6N-hydrochloric acid (1 l), followed by agitating the mixture, cooling it with ice, adding sodium nitrite (80 g), agitating the mixture at 0° C. for 3 hours, adding ether (300 ml), separating the resulting organic layer, extracting the aqueous layer with ether (150 ml), combining the organic layers, drying over MgSO4, distilling off ether and distilling the residue under reduced pressure, to obtain (2S,3S)-2-chloro-3-methylvaleric acid (34.2 g, b.p. 96-97/4 mmHg).

(ii) Preparation of the objective compound

In dichloromethane (300 ml) were dissolved (S)-1-(4'-octyloxy-4-biphenylyl)-propan-2-ol (8.0 g), DCC (15.0 g) and DMAP (2.0 g), followed by adding to the solution, (2S,3S)-2-chloro-3-methylvaleric acid (9.0 g) obtained in the above (i), agitating the mixture at room temperature for 6 hours, filtering off deposited crystals, washing the resulting organic layer with 6N-hydrochloric acid, washing the organic layer with water until the washing water became neutral, distilling off the organic layer and recrystallizing the residue from ethanol to obtain the objective 4'-octyloxy-4-(2'-(2''-chloro-3''-methylvalerylyloxy)-propoxy)biphenyl (4.0 g, m.p. 69.7° C.).

EXAMPLE 3

Preparation of 4'-octyloxy-4-(2'-(2''-propoxypropionyloxy)-propoxy)-biphenyl (a compound of the formula (I) wherein $R^1$=octyloxy group;

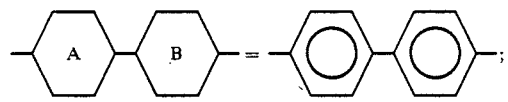

$l=1$; $m=0$; and

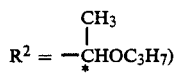

(i) Preparation of 2-propoxypropionic acid

Silver oxide (87.5 g, 0.38 mol) was added to a mixture of (R)-methyl lactate (52.1 g, 0.5 mol) with 1-iodopropane (100 g, 0.59 mol) over 3 hours, followed by allowing the mixture to stand at room temperature for 4 days, adding ether (200 ml) for dilution, filtering the mixture, distilling off ether, washing the residue with 2N-NaOH aqueous solution, drying over anhydrous sodium sulfate, distilling it under reduced pressure to obtain (R)-methyl 2-propoxypropionate (46.1 g, b.p. 33°-34° C./5 mmHg). To this (R)-methyl 2-propoxypropionate (28.2 g) were added water (60 ml) and NaOH (10 g), followed by agitating the mixture at room temperature for 3 hours, pouring the mixture in 6N-hydrochloric acid (80 ml), extracting the resulting organic layer with ether, washing the resulting organic layer with water and distilling off ether to obtain 2-propoxypropionic acid (18.0 g).

(ii) Preparation of the objective compound

To dichloromethane (500 ml) were added DCC (13.0 g, 0.06 mol), DMAP (2.0 g) and (S)-1-(4'-octyloxy-4-biphenylyloxy)-propan-2-ol (7.0 g), followed by adding to the mixture, 2'-propoxypropionic acid (7.0g) obtained in (i), agitating the mixture at room temperature for 4 hours, filtering off deposited crystals, washing the filtrate with 6N-hydrochloric acid, then with 2N-NaOH aqueous solution and further with water until the washing water became neutral, distilling off dichloromethane and recrystallizing the residue from ethanol, to obtain the objective compound, i.e.,4'-octyloxy-4-(2'-(2''-propoxypropionyloxy)-propoxy)biphenyl (1.5 g, m.p. 52.0° C.).

EXAMPLE 4

Preparation of 5-nonyl-2-(4'-(2''-(2'''-propoxypropionyloxy)-propoxy)-phenyl)pyridine (a compound of the formula (I) wherein $R^1$=nonyl group;

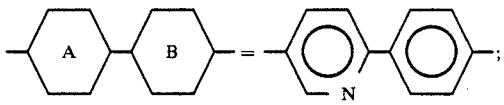

$l=1$; $m=0$; and $R^2$ represents

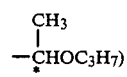

(S)-5-nonyl-2-(4'-(2''-hydroxypropoxy)phenyl)pyridine (m.p. 77.6°-80.3° C.) was reacted with 2-propoxypropionic acid prepared in Example 3 in the same manner as in Example 3 to obtain 5-nonyl-2-(4'-(2''-(2'''-propoxypropionyloxy)-propoxy)phenyl)pyridine (m.p. 58.0° C.).

The physical properties (m.p.) of compounds of Examples 1 to 4 and other compounds of the formula (I) similarly obtained are collectively shown in Table 1.

TABLE 1

| | | In formula (I) | | | | | | |
|---|---|---|---|---|---|---|---|---|
| Sample No. | $R^1$ | –⟨A⟩–⟨B⟩– | l | m | $R^2$ | Absolute configuration | M.P. (°C.) | Note |
| 1 | $C_8H_{17}O-$ | –⟨phenyl⟩–⟨phenyl⟩– | 1 | 0 | $-\overset{*}{C}H(CH_3)O-C_3H_7$ | S,R | 40.5 | |
| 2 | $C_6H_{13}O-$ | –⟨phenyl⟩–⟨phenyl⟩– | 1 | 0 | $-\overset{*}{C}H(CH_3)O-C_3H_7$ | S,R | 43.8 | |
| 3 | $C_8H_{17}O-$ | –⟨phenyl⟩–⟨phenyl⟩– | 1 | 0 | $-\overset{*}{C}H(CH_3)O-C_3H_7$ | S,S | 52.3 | Example 3 |
| 4 | $C_8H_{17}O-$ | –⟨phenyl⟩–⟨phenyl⟩– | 1 | 0 | $-\overset{*}{C}H(CH_3)O-C_3H_7$ | S,R | 52.0 | |
| 5 | $C_8H_{17}-$ | –⟨phenyl⟩–⟨phenyl⟩– | 1 | 0 | $-\overset{*}{C}H(CH_3)O-C_4H_9$ | S,S | 25.8 | |
| 6 | $C_8H_{17}O-$ | –⟨phenyl⟩–⟨phenyl⟩– | 1 | 0 | $-\overset{*}{C}H(CH_3)O-C_4H_9$ | S,S | 50.0 | Example 1 |
| 7 | $C_8H_{17}O-$ | –⟨phenyl⟩–⟨phenyl⟩– | 1 | 0 | $-\overset{*}{C}H(CH_3)O-C_4H_9$ | S,R | 41.0 | Example 1 |
| 8 | $C_{11}H_{23}O-$ | –⟨phenyl⟩–⟨phenyl⟩– | 1 | 0 | $-\overset{*}{C}H(CH_3)O-C_4H_9$ | S,S | 57.6 | |
| 9 | $C_{10}H_{21}O-$ | –⟨phenyl⟩–⟨phenyl⟩– | 1 | 0 | $-\overset{*}{C}H(CH_3)O-C_6H_{13}$ | S,S | 50.2 | |
| 10 | $C_8H_{17}O-$ | –⟨phenyl⟩–⟨phenyl⟩– | 1 | 0 | $-\overset{*}{C}H(Cl)-\overset{*}{C}H(CH_3)-CH_2CH_3$ | S,S,S | 69.7 | Example 2 |
| 11 | $C_8H_{17}O-$ | –⟨phenyl⟩–⟨phenyl⟩– | 1 | 1 | $-\overset{*}{C}H(CH_3)O-C_4H_9$ | R,R | 42.6 | |
| 12 | $C_8H_{17}O-$ | –⟨phenyl⟩–⟨phenyl⟩– | 2 | 0 | $-\overset{*}{C}H(CH_3)O-C_6H_{13}$ | R,S | 25.3 | |

TABLE 1-continued

| | | In formula (I) | | | | | | |
|---|---|---|---|---|---|---|---|---|
| Sample No. | $R^1$ | A—B | l | m | $R^2$ | Absolute configuration | M.P. (°C.) | Note |
| 13 | $C_{12}H_{25}-$ | phenyl-phenyl (with F) | 1 | 1 | $-\overset{*}{C}H(CH_3)O-C_4H_9$ | S,S | 27.7 | |
| 14 | $C_9H_{19}-$ | pyridyl-phenyl | 1 | 0 | $-\overset{*}{C}H(CH_3)O-C_3H_7$ | S,R | 53.0 | Example 4 |
| 15 | $C_9H_{19}-$ | pyridyl-phenyl | 1 | 0 | $-\overset{*}{C}H(CH_3)O-C_5H_{11}$ | S,S | 25.8 | |
| 16 | $C_8H_{17}-$ | pyridyl-phenyl | 1 | 1 | $-\overset{*}{C}H(Cl)-\overset{*}{C}H(CH_3)-CH_2CH_3$ | S,S,S | 34.3 | |
| 17 | $C_8H_{17}-$ | pyridazinyl | 1 | 0 | $-\overset{*}{C}H(CH_3)O-C_4H_9$ | S,S | 16.5 | |
| 18 | $C_8H_{17}O-$ | cyclohexyl-pyrimidinyl | 1 | 0 | $-\overset{*}{C}H(CH_3)O-C_4H_9$ | S,S | 45.0 | |
| 19 | $C_8H_{17}O-$ | cyclohexyl-pyrimidinyl | 1 | 0 | $-\overset{*}{C}H(CH_3)O-C_4H_9$ | S,R | 29.4 | |
| 20 | $C_8H_{17}-$ | phenyl-pyrimidinyl | 1 | 0 | $-\overset{*}{C}H(Cl)-\overset{*}{C}H(CH_3)-CH_2CH_3$ | S,S,S | 48.1 | |
| 21 | $C_8H_{17}-$ | phenyl-pyrimidinyl | 1 | 1 | $-\overset{*}{C}H(CH_3)O-C_3H_7$ | R,S | 35.2 | |
| 22 | $C_8H_{17}-$ | pyrimidinyl-phenyl (with F) | 1 | 0 | $-\overset{*}{C}H(CH_3)-O-C_3H_7$ | S,S | 22.1 | |
| 23 | $C_9H_{19}-$ | phenyl-phenyl (N—N) | 1 | 0 | $-\overset{*}{C}H(CH_3)-O-C_3H_7$ | S,S | 61.0 | |

TABLE 1-continued

| | In formula (I) | | | | | | |
|---|---|---|---|---|---|---|---|
| Sample No. | R¹ | —(A)—(B)— | l | m | R² | Absolute configuration | M.P. (°C.) | Note |
| 24 | $C_9H_{19}$— | phenyl-N=N-phenyl | 1 | 0 | $-\overset{*}{\underset{|}{C}H}-O-C_3H_7$ with $CH_3$ | S,R | 25.0 | |
| 25 | $C_8H_{17}O$— | phenyl-N=N-phenyl | 1 | 0 | $-\overset{*}{\underset{|}{C}H}-\overset{*}{\underset{|}{C}H}-CH_2CH_3$ with Cl, $CH_3$ | S,S,S | 74.4 | |
| 26 | $C_5H_{11}$— | H-phenyl | 1 | 0 | $-\overset{*}{\underset{|}{C}HO}-C_3H_7$ with $CH_3$ | S,S | 14.0 | |

EXAMPLE 5 (Use example 1)

A composition consisting of the following six kinds of achiral compounds and having SC phase was prepared:

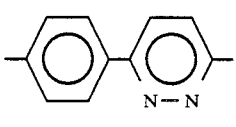 30 wt. %

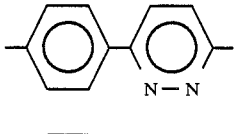 20 wt. %

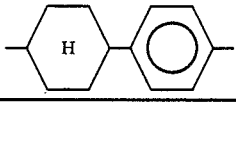 10 wt. %

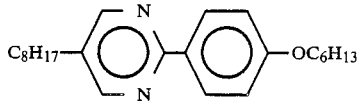 10 wt. %

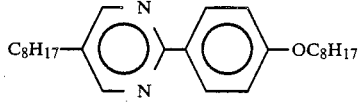 20 wt. %

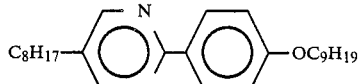 10 wt. %

The phase transition points of this composition were as follows:

$$C \xrightarrow{4°\ C.} SC \xrightarrow{65°\ C.} SA \xrightarrow{79°\ C.} N \xrightarrow{90°\ C.} I$$

When a compound of sample No. 6 as a compound of the formula (I) of the present invention was added in an amount of 10% by weight to the above composition, SC* phase exhibiting ferroelectric properties within a temperature range of 16° to 50° C. appeared. This composition had a spontaneous polarization value of 9.4 nC/cm² at 25° C. and a tilt angle of 16.7°. The composition was filled in a cell of 2 μm thickness provided with transparent electrodes each obtained by coating the surface with PVA as an aligning agent and rubbing the resulting surface to subject it to a parallel aligning treatment, followed by placing the resulting cell between two sheets of crossed polarizers and impressing thereto a square wave of ±10 V. As a result, change in the intensity of transmitted light was observed. The response time was sought from the change in the intensity of transmitted light at that time to give 100 μsec at 25° C.

From the foregoing, it is seen that when the compound of the present invention is used, it is possible to impart a spontaneous polarization to an achiral smectic composition and there is obtained a ferroelectric liquid crystal composition which has a high response rate at room temperature.

EXAMPLE 6

A chiral nematic liquid crystal composition, obtained by adding a compound of sample No. 6 in an amount of 1% by weight to ZLI-1132 manufactured by Merck Company was subjected to measurement of its chiral pitch according to Cano wedge method to give 15 μm at 25° C. Further, the temperature-dependency of pitch δP expressed by the formula $$\delta P = \frac{2(P(t_1) - P(t_2))}{P(t_1) + P(t_2)} \times \frac{100}{t_1 - t_2}$$

was 0.478 when $t_1 = 20°$ C. and $t_2 = 60°$ C.

What we claim is:

1. An optically active compound expressed by the formula

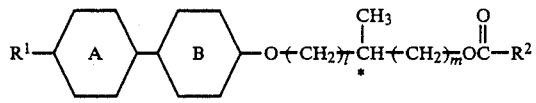 (I)

wherein R¹ represents a linear or branched chain alkyl group or alkoxy group, each of 5 to 12 carbon atoms; R² represents

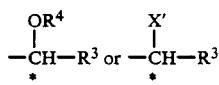

wherein R³ represents a linear or branched chain alkyl group, each of 1 to 15 carbon atoms, and when R³ represents a branched chain alkyl group it may be an optically active group, and R⁴ represents a linear or branched chain alkyl group, each of 1 to 10 carbon atoms, and when R⁴ represents a branched chain alkyl group, it may be an optically active group, and X' represents F, Cl or Br;

is biphenyl or fluoro-substituted biphenyl,
l represents an integer of 1 or 2;
m represents 0; and
* indicates an asymmetric carbon atom.

2. A liquid crystal composition comprising at least two components, at least one of which is an optically active compound as set forth in claim 1.

3. A liquid crystal composition according to claim 2, exhibiting a chiral smectic liquid crystal phase.

4. A liquid crystal composition according to claim 2, exhibiting a chiral nematic liquid crystal phase.

5. A liquid crystal display element containing a liquid crystal composition as set forth in claim 2.

6. An optically active compound according to claim 1, wherein

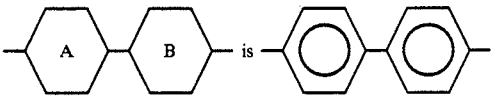

7. An optically active compound according to claim 6, wherein R² is

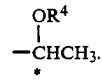

8. An optically active compound expressed by the formula

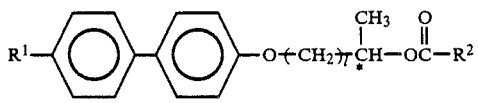

wherein R¹ represents a linear or branched alkoxy group of 5 to 12 carbon atoms; R² represents

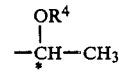

wherein R⁴ represents a linear or branched chain alkyl group of 1 to 10 carbon atoms; l represents an integer of 1 or 2; and * indicates an asymmetric carbon atom.

* * * * *